(12) United States Patent
Cosmescu

(10) Patent No.: US 11,540,870 B2
(45) Date of Patent: Jan. 3, 2023

(54) ULTRAPOLAR ELECTROSURGERY BLADE ASSEMBLY AND ULTRAPOLAR ELECTROSURGERY PENCIL WITH ARGON BEAM CAPABILITY

(71) Applicant: I.C. Medical, Inc., Phoenix, AZ (US)

(72) Inventor: Ioan Cosmescu, Phoenix, AZ (US)

(73) Assignee: I.C. Medical, Inc., Phoenix, AZ (US)

( * ) Notice: Subject to any disclaimer, the term of this patent is extended or adjusted under 35 U.S.C. 154(b) by 357 days.

(21) Appl. No.: 16/715,962

(22) Filed: Dec. 16, 2019

(65) Prior Publication Data
US 2020/0113618 A1  Apr. 16, 2020

Related U.S. Application Data

(63) Continuation of application No. 15/648,553, filed on Jul. 13, 2017, now Pat. No. 10,507,053.

(60) Provisional application No. 62/362,873, filed on Jul. 15, 2016.

(51) Int. Cl.
| | | |
|---|---|---|
| *A61B 18/14* | (2006.01) | |
| *A61B 18/04* | (2006.01) | |
| *A61M 13/00* | (2006.01) | |
| *A61B 17/00* | (2006.01) | |
| *A61B 18/00* | (2006.01) | |
| *A61B 18/12* | (2006.01) | |

(52) U.S. Cl.
CPC ........ *A61B 18/1402* (2013.01); *A61B 18/042* (2013.01); *A61B 18/14* (2013.01); *A61M 13/003* (2013.01); *A61B 2017/00991* (2013.01); *A61B 2018/00077* (2013.01); *A61B 2018/00083* (2013.01); *A61B 2018/00589* (2013.01); *A61B 2018/00601* (2013.01); *A61B 2018/00607* (2013.01); *A61B 2018/1246* (2013.01); *A61B 2018/1412* (2013.01); *A61B 2218/005* (2013.01); *A61B 2218/007* (2013.01); *A61B 2218/008* (2013.01)

(58) Field of Classification Search
CPC ... A61B 18/042; A61B 18/14; A61B 18/1402; A61B 2017/00991; A61B 2018/00077; A61B 2018/00083; A61B 2018/00589; A61B 2018/00601; A61B 2018/00607; A61B 2018/1246; A61B 2018/1412; A61B 2218/005; A61B 2218/007; A61B 2218/008; A61M 13/003
See application file for complete search history.

(56) References Cited

U.S. PATENT DOCUMENTS

| | | | |
|---|---|---|---|
| 3,970,088 A * | 7/1976 | Morrison | A61B 18/1402 606/48 |
| 4,674,498 A | 6/1987 | Stasz | |
| 5,013,312 A * | 5/1991 | Parins | A61B 18/1402 606/37 |

(Continued)

FOREIGN PATENT DOCUMENTS

| | | |
|---|---|---|
| WO | 2000/028908 A1 | 5/2000 |
| WO | 2014/138366 A1 | 9/2014 |

*Primary Examiner* — Michael F Peffley
(74) *Attorney, Agent, or Firm* — Zeman-Mullen & Ford LLP

(57) ABSTRACT

An ultrapolar electrosurgery blade assembly with argon beam capability and an ultrapolar electrosurgery pencil with argon beam capability that are both capable of using monopolar energy in a bipolar mode for cutting and coagulation and using ionized gas for cutting and coagulation.

20 Claims, 4 Drawing Sheets

(56) References Cited

U.S. PATENT DOCUMENTS

| | | | |
|---|---|---|---|
| 5,256,138 A | 10/1993 | Burek et al. | |
| 5,281,216 A | 1/1994 | Klicek | |
| 7,150,748 B2 * | 12/2006 | Ebbutt | A61B 18/1402 |
| | | | 606/50 |
| 2007/0191759 A1 * | 8/2007 | Stoller | A61B 1/3132 |
| | | | 604/22 |
| 2013/0110108 A1 | 5/2013 | Davison et al. | |
| 2015/0196353 A1 * | 7/2015 | Hancock | A61B 18/1815 |
| | | | 606/46 |
| 2016/0317209 A1 * | 11/2016 | Cosmescu | A61B 18/1402 |

* cited by examiner

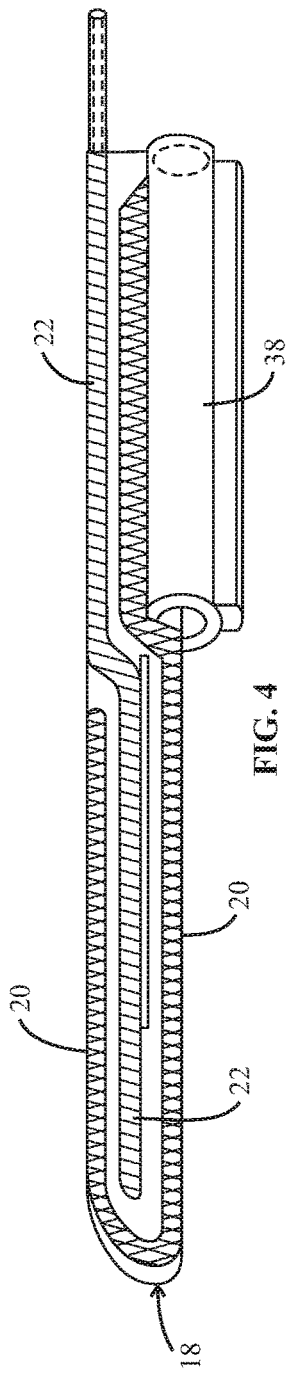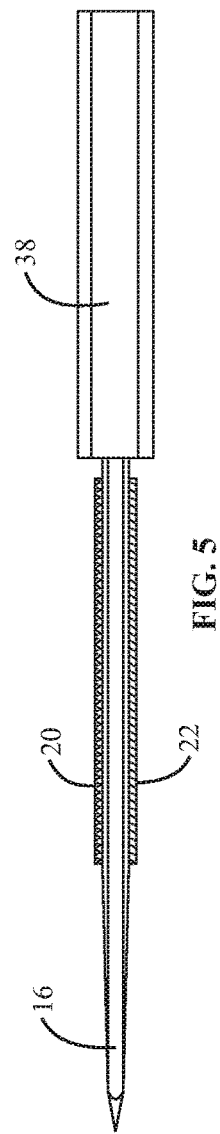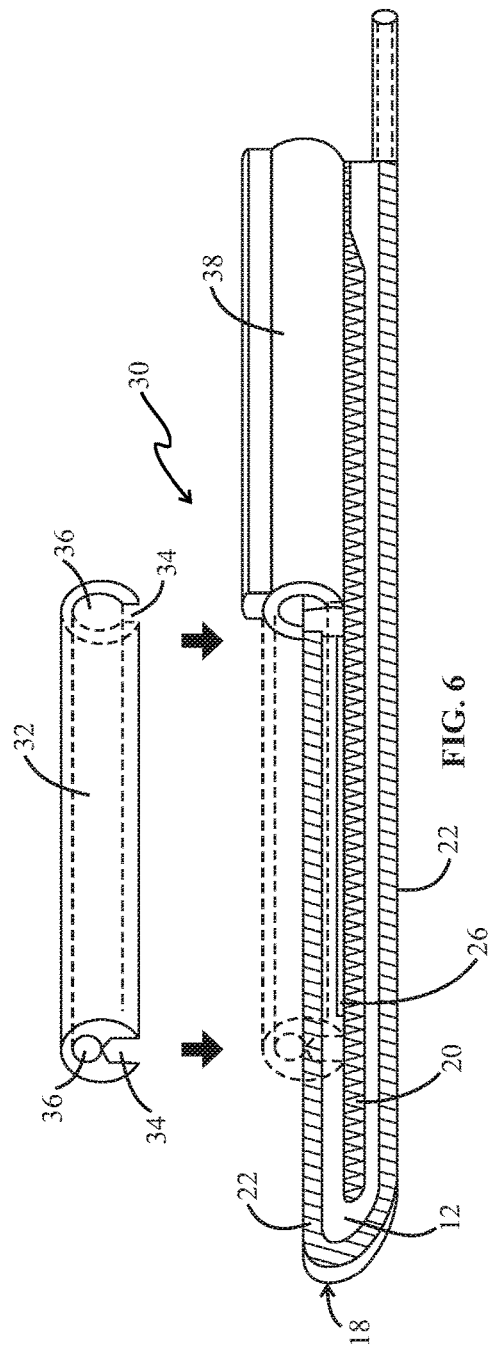

ULTRAPOLAR ELECTROSURGERY BLADE ASSEMBLY AND ULTRAPOLAR ELECTROSURGERY PENCIL WITH ARGON BEAM CAPABILITY

CROSS-REFERENCE TO RELATED APPLICATIONS

This application is a continuation of and claims benefit of priority to U.S. Nonprovisional Patent Application having Ser. No. 15/648,553 filed Jul. 13, 2017, issued as U.S. Pat. No. 10,507,053, which claims priority to provisional patent application having Ser. No. 62/362,873, filed Jul. 15, 2016, which are herein incorporated by reference in its entireties.

FIELD OF INVENTION

The present invention is generally directed to an ultrapolar electrosurgery blade assembly having argon beam capability and an ultrapolar electrosurgery pencil with argon beam capability. Both are capable of using monpolar energy in a bipolar mode for cutting and coagulation and both are capable of using an ionized gas for cutting and coagulation.

BACKGROUND OF THE INVENTION

Electrosurgery uses an RF electrosurgical generator (also known as an electrosurgical unit or ESU) and a handpiece with an electrode to provide high frequency, alternating radio frequency (RF) current input at various voltages to cut or coagulate biological tissue. The handpiece may be a monopolar instrument with one electrode or a bipolar instrument with two electrodes. When using a monopolar instrument, a return electrode pad is attached to the patient and the high frequency electrical current flows from the generator, to the monopolar instrument, through the patient to the patient return electrode pad, and back to the generator. Monopolar electrosurgery is commonly used due to its versatility and effectiveness. However, the excessive heat generated with monopolar electrosurgery can cause excessive tissue damage and necrosis of the tissue because the return electrode positioned on the back of the patient causes high voltage and high RF energy to pass through the patient.

In bipolar electrosurgery, active output and patient return functions both occur at the surgery site because both the active and return electrodes are contained in the bipolar instrument. Therefore, the path of the electrical current is confined to the biological tissue located between the active and return electrodes. Although bipolar electrosurgery enables the use of lower voltages and less energy than monopolar electrosurgery and thereby reduces or eliminates the likelihood of tissue damage and sparking associated with monopolar electrosurgery, it has limited ability to cut and coagulate large bleeding areas.

It is also common to use argon beam coagulators during electrosurgery. In argon beam coagulation (ABC), current is applied to tissue by a directed beam of ionized argon gas which causes a uniform and shallow coagulation surface thereby stopping blood loss. However, argon beam enhanced cutting may also be performed using application of an ionized argon gas.

At present, electrosurgery is often the best method for cutting and argon beam coagulation is often the best method for cessation of bleeding during surgery. Surgeons typically need to switch between argon beam coagulation and electrosurgery modes depending on what is happening during the surgery and what they need to achieve at a particular point in the surgery such as cutting, or making incisions in tissue, or stopping the bleeding at the surgical site.

However, since surgical tools and devices currently available to surgeons require switching between these two methods during the surgical procedure, there is a need for a surgical device or tool that enables a surgeon or user to utilize the best methods used for cutting and cessation of bleeding at the surgical site at the same time, or simultaneously, in addition to being able to use them separately. An electrosurgery blade assembly with argon beam capability and an electrosurgery pencil with argon beam capability that utilizes such an electrosurgery blade assembly can provide a user or surgeon with safe, efficient, effective, and flexible ways to both cut and coagulate tissue during electrosurgery.

SUMMARY OF THE INVENTION

The present invention is directed to an ultrapolar electrosurgery blade assembly having argon beam capability and an ultrapolar electrosurgery pencil with argon beam capability that are both capable of using monopolar energy in a bipolar mode for cutting and coagulation using an electrosurgery blade. The ultrapolar electrosurgery blade assembly having argon beam capability and the ultrapolar electrosurgery pencil with argon beam capability of the present invention are also both capable of using an ionized gas for cutting and coagulation thereby providing a user or surgeon with a variety of ways to perform cutting and/or coagulation of tissue during an operative procedure.

In one exemplary embodiment, the ultrapolar electrosurgery blade assembly having argon beam capability of the present invention includes a non-conductive blade having opposing planar sides, a narrow elongated top, a sharp cutting end, and an opposite non-cutting end; both an active electrode or active contact and a return electrode or return contact (note that the terms electrode and contact are used interchangeably throughout this specification) located on each of the opposing planar sides of the non-conductive blade, and a non-conductive hollow tubular member positioned over the narrow elongated top of the non-conductive blade so that the non-conductive hollow tubular member covers at least a portion of an active electrode/contact on one of the opposing planar sides of the non-conductive blade and at least a portion of a return electrode/contact on the other opposing planar side of the non-conductive blade. This enables a gas supplied to the non-conductive hollow tubular member to be ionized as it comes into contact with the active and return electrodes/contacts contained within the non-conductive hollow tubular member thereby enabling both cutting and coagulation of tissue without high voltage and high RF energy passing through the patient.

In another exemplary embodiment, a second non-conductive hollow tubular member may also be included as part of the ultrapolar electrosurgery blade assembly of the present invention by positioning it adjacent to the previously described non-conductive hollow tubular member that is positioned over at least a portion of both active and return contacts located on opposite sides of the electrosurgery blade. In this embodiment, the second non-conductive hollow tubular member may also be positioned and fixed over the electrosurgery blade (but not necessarily positioned over both active and return contacts on the electrosurgery blade) and the previously described non-conductive hollow tubular member may be supported in its position over at least a portion of the active and return contacts of the electrosurgery blade by seating it on a non-conductive shelf support located on the electrosurgery blade. This enables the non-conductive hollow tubular member that is positioned over at least a portion of active and return contacts of the electrosurgery blade to be changeable/replaceable. The non-conductive hollow tubular member that is positioned over at least a portion of active and return contacts of the electrosurgery blade may also be permanently attached to the second non-conductive hollow tubular member and/or the non-conductive shelf support. The non-conductive hollow tubular member may include a slot which fits over at least a portion of the electrosurgery blade and an opening located above the slot through which an ionized gas can project after coming into contact with the active and return contacts of the electrosurgery blade contained within the non-conductive hollow tubular member.

The ultrapolar electrosurgery blade assembly having argon beam capability of the present invention may also include a non-conductive support member connected to the non-conductive blade for retaining the ultrapolar electrosurgery blade assembly within an electrosurgery handpiece. The non-conductive support member may also be attached to one or both of the non-conductive hollow tubular members.

In still another exemplary embodiment, the ultrapolar electrosurgery handpiece having argon beam capability of the present invention includes a handpiece member having a first end and a second end, a non-conductive blade positioned within the first end of the handpiece member where the non-conductive blade includes opposing planar sides, a sharp cutting end, and both an active contact and a return contact located on each of the opposing planar sides of the non-conductive blade, a non-conductive hollow tubular member positioned on the non-conductive blade so that it covers at least a portion of an active contact on one opposing planar side of the non-conductive blade and at least a portion of a return contact on the other opposing planar side of the non-conductive blade, and a non-conductive tube positioned within the handpiece member and connected to the non-conductive hollow tubular member for supplying a gas to the non-conductive hollow tubular member. The handpiece member can include a channel for evacuating smoke and/or debris away from the sharp cutting end of the non-conductive blade and the ultrapolar electrosurgery pencil with argon beam capability may also include a rotating/swivel member connected to the second end of the handpiece member.

The exemplary embodiments of the electrosurgery blade assembly with argon beam capability and the electrosurgery pencil with argon beam capability of the present invention enable a user or surgeon to perform cutting with the sharp non-conductive tip of the electrosurgery blade, cutting with the active and return electrodes/contacts of the electrosurgery blade, coagulating large areas of biological tissue by placing the electrosurgery blade on either of its sides where both active and return electrodes/contacts are located, and cutting and coagulating tissue using ionized gas that projects from the non-conductive hollow tubular shaped member that is positioned over active and return electrodes/contacts contained on the electrosurgery blade. A particularly new and innovative feature of the electrosurgery blade assembly with argon beam capability and the electrosurgery pencil with argon beam capability of the present invention is the ability of a user or surgeon to simultaneously cut tissue with the sharp non-conductive tip of the electrosurgery blade while coagulating tissue using ionized gas that projects from the non-conductive hollow tubular shaped member that is positioned over active and return electrodes/contacts contained on the electrosurgery blade. The electrosurgery blade assembly with argon beam capability and the electrosurgery pencil with argon beam capability of the present invention provide a user or surgeon with safe, efficient, effective, and flexible ways to both cut and coagulate tissue during electrosurgery. The electrosurgery blade assembly with argon beam capability and the electrosurgery pencil with argon beam capability of the present invention are much safer for the patient than other electrosurgery instruments and methods due to the fact that high voltage and high RF energy do not need to pass through the patient during electrosurgery.

BRIEF DESCRIPTION OF THE DRAWINGS

FIG. 4 is a perspective view of the exemplary embodiment of the ultrapolar electrosurgery blade assembly with argon beam capability depicted in FIG. 6 shown rotated 180 degrees without the first hollow non-conductive tubular member to show the active and return contacts/electrodes located on the opposite side of the ultrapolar electrosurgery blade;

FIG. 5 is a top plan view of the exemplary embodiment of the ultrapolar electrosurgery blade assembly with argon beam capability shown in FIG. 6 without the first non-conductive hollow tubular member;

FIG. 6 is an exploded perspective view of an exemplary embodiment of the ultrapolar electrosurgery blade assembly with argon beam capability of the present invention showing how the first hollow non-conductive tubular member is positioned over the electrosurgery blade;

DETAILED DESCRIPTION OF EXEMPLARY EMBODIMENTS

The ultrapolar electrosurgery blade assembly having argon beam capability and the ultrapolar electrosurgery pencil with argon beam capability of the present invention provide a user or surgeon with a variety of ways to perform cutting and/or coagulation of tissue during an operative procedure using electrosurgery. The ultrapolar electrosurgery blade assembly with argon beam capability and the ultrapolar electrosurgery pencil with argon beam capability are both capable of using monopolar energy in a bipolar mode for cutting and coagulation using an electrosurgery blade and are both capable of using an ionized gas for cutting and coagulation. The ultrapolar electrosurgery pencil with argon beam capability of the present invention may also provide the evacuation of smoke and debris away from the surgical site while using the electrosurgery blade and/or ionized gas for cutting and/or coagulation.

Figure 1:
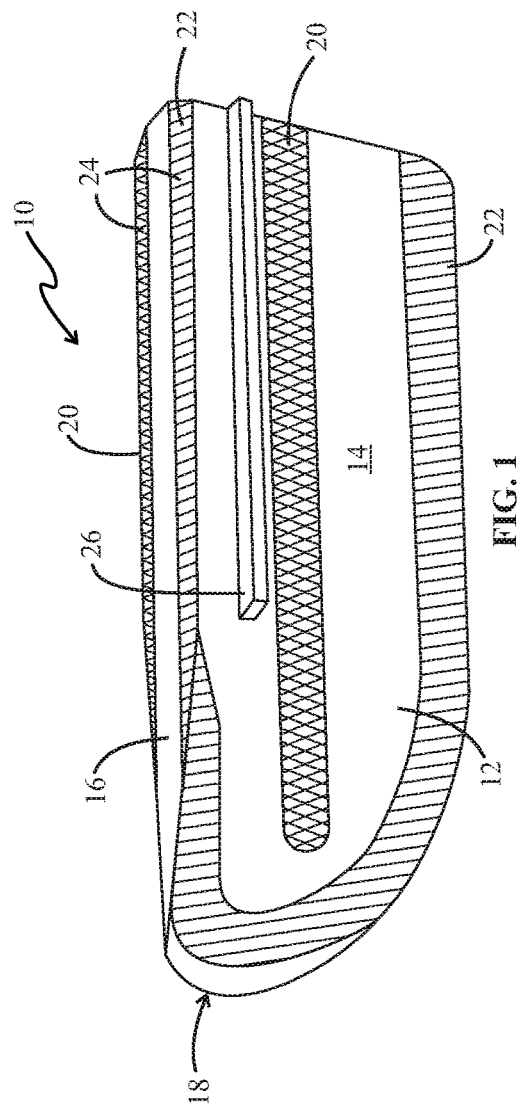
FIG. 1 is a partial perspective view of an exemplary embodiment of an ultrapolar electrosurgery blade that comprises part of an ultrapolar electrosurgery blade assembly with argon beam capability of the present invention.

FIG. 1 is a partial perspective view of an exemplary embodiment of an ultrapolar electrosurgery blade that comprises part of an ultrapolar electrosurgery blade assembly with argon beam capability of the present invention. Ultrapolar electrosurgery blade 10 includes a non-conductive blade 12 having opposing planar sides 14, a narrow elongated top 16, a sharp cutting end 18 and an opposite non-cutting end (not shown due to the partial view of the blade). Ultrapolar electrosurgery blade 10 also includes both an active electrode 20 and a return electrode 22 located on each of the opposing planar sides 14 of the non-conductive blade 12. Portions 24 of active electrode 20 and return electrode 22 that are located adjacent to the narrow elongated top 16 of non-conductive blade 12 reside on a part of non-conductive blade 12 that projects outward and downward from the narrow elongated top 16.

Figure 2:
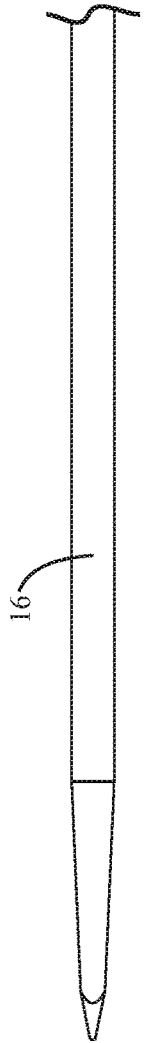
FIG. 2 is a top plan view of the exemplary embodiment of the ultrapolar electrosurgery blade shown in FIG. 1.

The ultrapolar electrosurgery blade 10 may also include a non-conductive shelf support 26 for supporting the non-conductive hollow tubular member that comprises part of the electrosurgery blade assembly with argon beam capability later shown and described with reference to FIGS. 6 and 7. A top plan view of the exemplary embodiment of the ultrapolar electrosurgery blade 10 shown in FIG. 1 is depicted in FIG. 2.

An exploded perspective view of an exemplary embodiment of the ultrapolar electrosurgery blade assembly with argon beam capability 30 of the present invention showing how the first hollow non-conductive tubular member 32 is positioned over the ultrapolar electrosurgery blade 10 is shown in FIG. 6. First non-conductive hollow tubular member 32 has a slot 34 which fits over the narrow elongated top 16 of the non-conductive blade 12 such that the non-conductive hollow tubular member 32 covers at least a portion of an active electrode 20 on one opposing planar side 14 of the non-conductive blade 12 and at least a portion of a return electrode 22 on the other opposing planar side 14 of the non-conductive blade 12. The non-conductive hollow tubular member 32 further includes an opening 36 located above the slot 34 on each end of the non-conductive hollow tubular member 32. This enables a gas supplied to the non-conductive hollow tubular member 32 to be ionized as it comes into contact with portions of the active and return electrodes contained within the non-conductive hollow tubular member 32 and the ionized gas is then projected through the opening 36 of the non-conductive hollow tubular member 32 that is located closest to the sharp cutting end 18 of the ultrapolar electrosurgery blade 10.

A second non-conductive hollow tubular member 38 may be positioned over the narrow elongated top 16 of the non-conductive blade 12 adjacent the first non-conductive hollow tubular member 32 but does not cover any portion of the active electrodes 20 and the return electrodes 22. The first non-conductive hollow tubular member 32 can be seated on the non-conductive shelf support 26 of the ultrapolar electrosurgery blade 10 and the first non-conductive hollow tubular member 32 may be changeable/replaceable. Alternatively, the first non-conductive hollow tubular member 32 may be permanently attached to the second non-conductive hollow tubular member 38 and/or the non-conductive shelf support 26.

Figure 3:
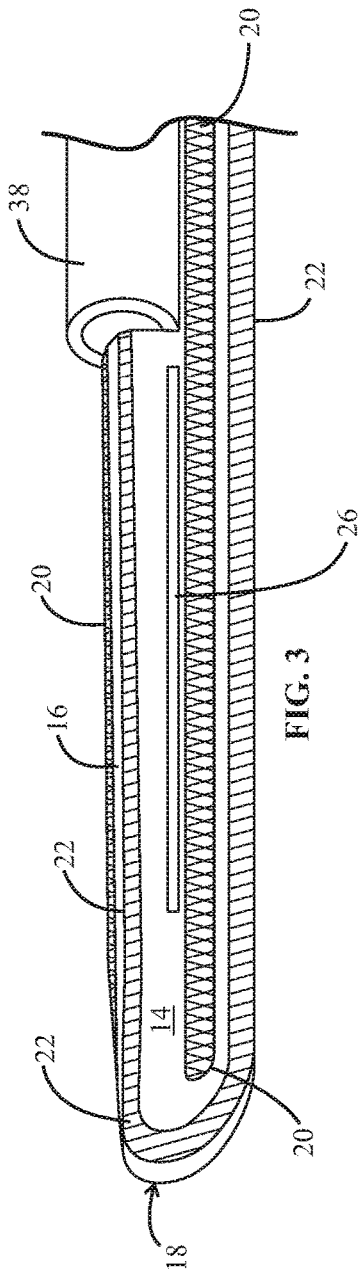
FIG. 3 is a partial perspective view of an exemplary embodiment of the ultrapolar electrosurgery blade assembly with argon beam capability of the present invention shown without a first hollow non-conductive tubular member positioned over the ultrapolar electrosurgery blade and supported by the shelf support (See FIGS. 6 and 7 to see first hollow non-conductive tubular member and seating of it on the shelf support)

A partial perspective view of an exemplary embodiment of the ultrapolar electrosurgery blade assembly with argon beam capability 30 of the present invention shown without the first hollow non-conductive tubular member 32 positioned over the ultrapolar electrosurgery blade 10 is shown in FIG. 3. FIG. 3 shows a partial view of what is depicted in FIG. 6 with a more close-up perspective view of the portion of the ultrapolar electrosurgery blade 10 that is covered when the first non-conductive hollow tubular member 32 is positioned over the ultrapolar electrosurgery blade 10. FIG. 4 is a perspective view of the exemplary embodiment of the ultrapolar electrosurgery blade assembly with argon beam capability depicted in FIG. 6 shown rotated 180 degrees without the first hollow non-conductive tubular member to show the active and return contacts/electrodes located on the opposite side of the ultrapolar electrosurgery blade. As shown in FIGS. 4 and 6, when the first non-conductive hollow tubular member 32 is seated over the narrow elongated top 16 of ultrapolar electrosurgery blade 10, the first non-conductive hollow tubular member 32 will cover a portion of return electrode/contact 22 on one opposing planar side 14 of non-conductive blade 12 (See FIG. 6) and a portion of active electrode/contact 20 on the other opposing planar side 14 of non-conductive blade 12 (See FIG. 4). FIG. 5 is a top plan view of the exemplary embodiment of the ultrapolar electrosurgery blade assembly with argon beam capability shown in FIG. 6 without the first non-conductive hollow tubular member.

The non-conductive blade 12 and the first non-conductive hollow tubular member 32 may each comprise a ceramic material. The second non-conductive hollow tubular member 38 may also comprise a ceramic material.

Figure 7:
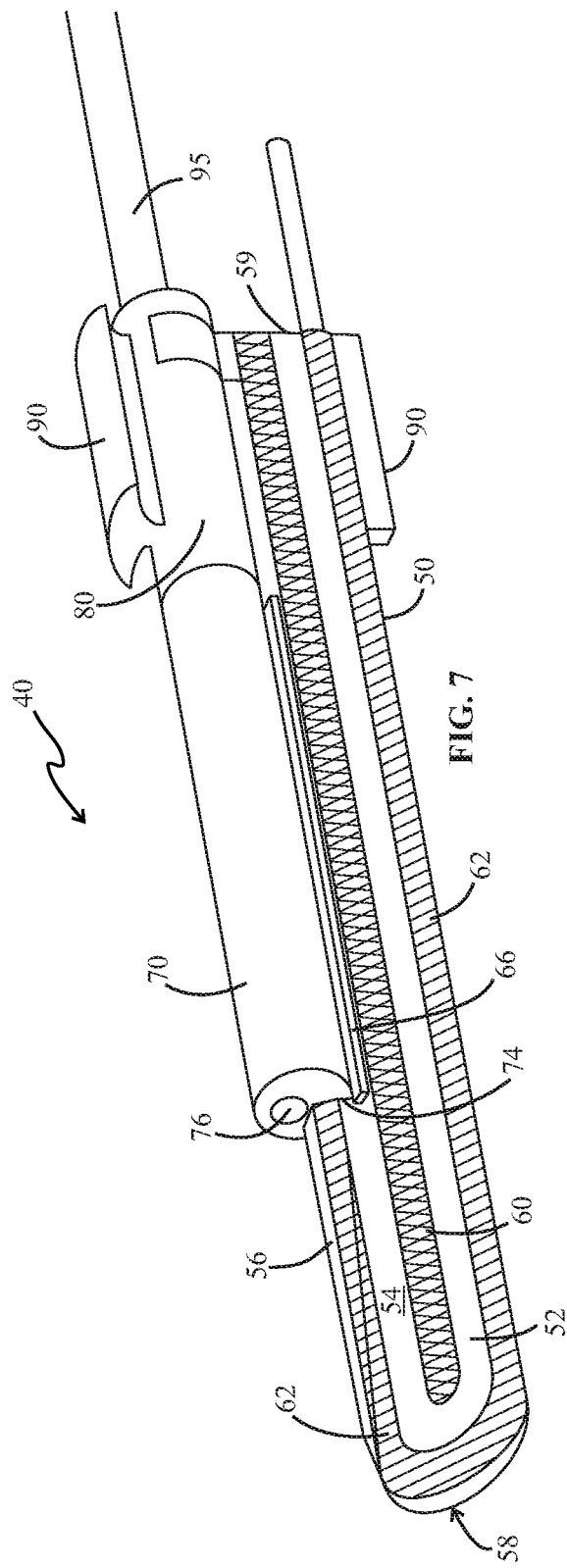
FIG. 7 is perspective view of another exemplary embodiment of the ultrapolar electrosurgery blade assembly with argon beam capability of the present invention.

FIG. 7 is perspective view of another exemplary embodiment of the ultrapolar electrosurgery blade assembly with argon beam capability 40 of the present invention. Ultrapolar electrosurgery blade assembly with argon beam capability 40 includes an ultrapolar electrosurgery blade 50, a first non-conductive hollow tubular member 70, and a second non-conductive hollow tubular member 80. Ultrapolar electrosurgery blade 50 includes a non-conductive blade 52 having opposing planar sides 54, a narrow elongated top 56, a sharp cutting end 58 and an opposite non-cutting end 59. Ultrapolar electrosurgery blade 50 also includes both an active electrode 60 and a return electrode 62 located on each of the opposing planar sides 54 of the non-conductive blade 52. Portions of active electrode 60 and return electrode 62 that are located adjacent to the narrow elongated top 56 of non-conductive blade 52 reside on a part of non-conductive blade 52 hat projects outward and downward from the narrow elongated top 56. The ultrapolar electrosurgery blade 50 may also include a non-conductive shelf support 66 for supporting the first non-conductive hollow tubular member 70 that is positioned over the ultrapolar electrosurgery blade 50. First non-conductive hollow tubular member 70 has a slot 74 which fits over the narrow elongated top 56 of the non-conductive blade 52 such that the non-conductive hollow tubular member 70 covers at least a portion of an active electrode 60 on one opposing planar side 54 of the non-conductive blade and at least a portion of a return electrode 62 on the other opposing planar side 54 of the non-conductive blade 52. The first non-conductive hollow tubular member 70 further includes an opening 76 located above the slot 74 on each end of the non-conductive hollow tubular member 70. This enables a gas supplied to the non-conductive hollow tubular member 70 to be ionized as it comes into contact with portions of the active and return electrodes contained within the non-conductive hollow tubular member 70 and the ionized gas is then projected through the opening 76 of the non-conductive hollow tubular member 70 that is located closest to the sharp cutting end 58 of the ultrapolar electrosurgery blade 50.

The second non-conductive hollow tubular member 80 may be positioned over the narrow elongated top 56 of the non-conductive blade 52 adjacent to the first non-conductive hollow tubular member 70 but does not cover any portion of the active electrodes 60 and the return electrodes 62. The first non-conductive hollow tubular member 70 can be seated on the non-conductive shelf support 66 of the ultrapolar electrosurgery blade 50 and the first non-conductive hollow tubular member 70 may be changeable/replaceable. Alternatively, the first non-conductive hollow tubular member 70 may be permanently attached to the second non-conductive hollow tubular member 80 and/or the non-conductive shelf support 66. The ultrapolar electrosurgery blade assembly with argon beam capability 40 further includes a non-conductive support member 90 connected to the ultrapolar electrosurgery blade 50 for retaining the ultrapolar electrosurgery blade assembly with argon beam capability within an electrosurgery handpiece. The non-conductive support member 90 may also be attached to one or both of the first and second non-conductive hollow tubular members 70, 80. In FIG. 7, the non-conductive support member 90 is shown attached to the ultrapolar electrosurgery blade 50 and the second non-conductive hollow tubular member 80. A non-conductive tube 95 is shown attached to second non-conductive hollow tubular member 80 to supply a gas to be ionized within the first non-conductive hollow tubular member 70.

Figure 8:
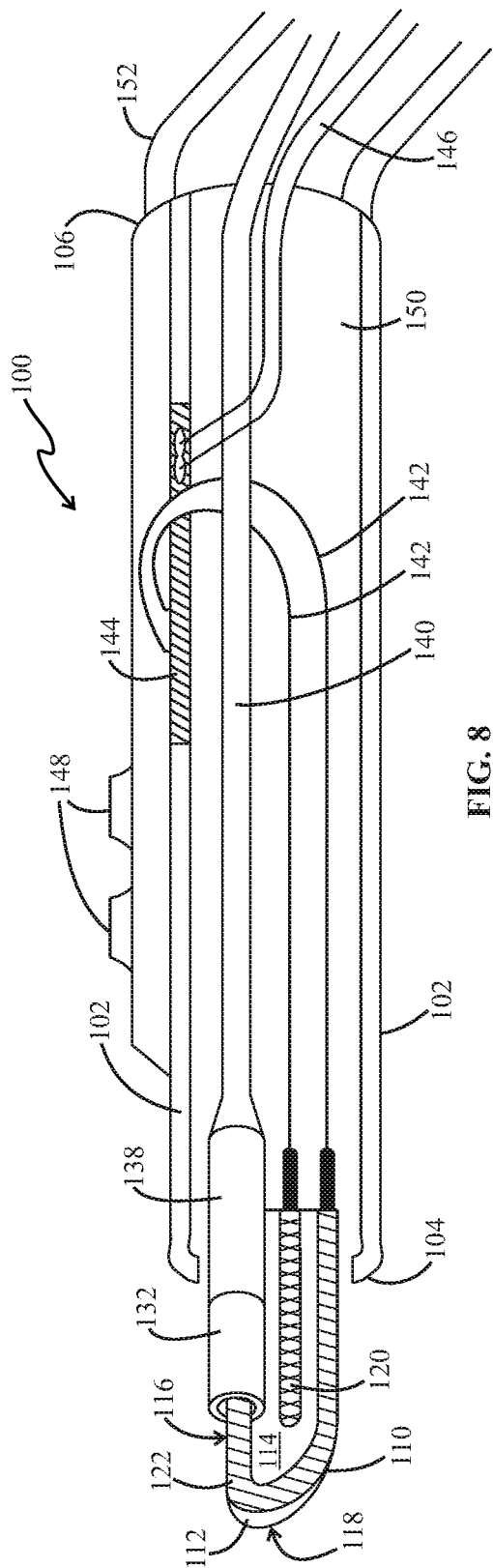
FIG. 8 is a side perspective view of an exemplary embodiment of the ultrapolar electrosurgery pencil with argon beam capability of the present invention showing a side of the handpiece portion of the electrosurgery pencil removed to show the interior of the electrosurgery pencil.

FIG. 8 is a side perspective view of an exemplary embodiment of the ultrapolar electrosurgery pencil with argon beam capability 100 of the present invention showing a side of the handpiece portion of the ultrapolar electrosurgery pencil 100 removed to show the interior of the ultrapolar electrosurgery pencil. The ultrapolar electrosurgery handpiece with argon beam capability 100 includes a handpiece member 102 having a first end 104 and a second end 106 and an ultrapolar electrosurgery blade 110 positioned within the first end 104 of the handpiece member 102. The ultrapolar electrosurgery blade 110 includes a non-conductive blade 112 having opposing planar sides 114, a narrow elongated top 116, and a sharp cutting end 118, and both an active contact 120 and a return contact 122 located on each of the opposing planar sides 114 of the non-conductive blade 112. A first non-conductive hollow tubular member 132 is positioned on the non-conductive blade 112 so that it covers at least a portion of an active contact 120 on one opposing planar side 114 of the non-conductive blade 112 and at least a portion of a return contact 122 on the other opposing planar side 114 of the non-conductive blade 112. The ultrapolar electrosurgery pencil with argon beam capability further includes a second non-conductive hollow tubular member 138 contained within the handpiece member 102 that is connected to the first non-conductive hollow tubular member 132, and a non-conductive tube 140 positioned within the handpiece member 102 and connected to the second non-conductive hollow tubular member 138 for supplying a gas to the first and second non-conductive hollow tubular members 132, 138. Wires 142 connect active contact 120 and return contact 122 to a circuit board 144 which is in turn connected to a power source via a power cord 146. Selection buttons 148 on handpiece member 102 are used to activate cutting and/or coagulation. The handpiece member can include a channel 150 for evacuating smoke and/or debris away from the sharp cutting end 118 of the non-conductive blade 112 and the ultrapolar electrosurgery pencil with argon beam capability 100 may also include a rotating/swivel member 152 connected to the second end 106 of the handpiece member 102 to alleviate drag and kinking of the suction tube when operating the ultrapolar electrosurgery pencil with argon beam capability 100 with a vacuum for smoke evacuation. Any of the previously discussed embodiments of the ultrapolar electrosurgery blade assembly with argon beam capability may be used with the ultrapolar electrosurgery pencil with argon beam capability of the present invention including an ultrapolar electrosurgery blade assembly that only has a first non-conductive hollow tubular member positioned over portions of active and return contacts located on opposite sides of the ultrapolar electrosurgery blade.

It will be understood by those skilled in the art that the active and return electrodes/contacts as depicted in all of the drawing figures may be reversed—i.e. the contacts shown as active contacts could be return contacts and the contacts shown as return contacts could be active contacts since both opposing planar sides of the non-conductive electrosurgery blade have both active and return contacts that mimic the configuration of one another. Reversing the types of electrodes/contacts would still result in the ultrapolar electrosurgery blade assembly with argon beam capability and the ultrapolar electrosurgery pencil with argon beam capability having the same functional features and advantages. The terms "electrode" and "contact" are meant to be used interchangeably throughout the specification.

The above description of exemplary embodiments of the invention shows various exemplary embodiments of the invention. These exemplary embodiments and modes are described and shown in sufficient detail to enable those skilled in the art to practice the invention and are not intended to limit the scope, applicability, or configuration of the invention in any way. Rather, the disclosure is intended to teach both the implementation of the exemplary embodiments and modes and any equivalent modes or embodiments that are known or obvious to those reasonably skilled in the art. Additionally, all included examples are non-limiting illustrations of the exemplary embodiments and modes, which similarly avail themselves to any equivalent modes or embodiments that are known or obvious to those reasonably skilled in the art.

Other combinations and/or modifications of structures, arrangements, applications, proportions, elements, materials, or components used in the practice of the instant invention, in addition to those not specifically recited, can be varied or otherwise particularly adapted to specific environments, manufacturing specifications, design parameters, or other operating requirements without departing from the scope of the instant invention and are intended to be included in this disclosure.

Unless specifically noted, it is the Applicant's intent that the words and phrases in the specification and the claims be given the commonly accepted generic meaning or an ordinary and accustomed meaning used by those of ordinary skill in the applicable arts. In the instance where these meanings differ, the words and phrases in the specification and the claims should be given the broadest possible, generic meaning. If any other special meaning is intended for any word or phrase, the specification will clearly state and define the special meaning.

The invention claimed is:

1. An ultrapolar electrosurgery blade assembly comprising:
   a non-conductive blade having opposing planar sides, a narrow elongated top, a sharp cutting end, and an opposite non-cutting end;

both an active contact and a return contact located on each of the opposing planar sides of the non-conductive blade;

a non-conductive hollow tubular member positioned over the narrow elongated top of the non-conductive blade; and a non-conductive support member connected to the non-conductive blade for retaining the ultrapolar electrosurgery blade assembly within an electrosurgery handpiece.

2. The ultrapolar electrosurgery blade assembly of claim 1 wherein the narrow elongated top of the non-conductive blade separates an active contact on one opposing planar side of the non-conductive blade and a return contact on the other opposing side of the non-conductive blade.

3. The ultrapolar electrosurgery blade assembly of claim 1 further comprising a second non-conductive hollow tubular member positioned over the narrow elongated top of the non-conductive blade adjacent to the non-conductive hollow tubular member.

4. The ultrapolar electrosurgery blade assembly of claim 1 further comprising a non-conductive shelf support for supporting the non-conductive hollow tubular member when positioned over the narrow elongated top of the non-conductive blade.

5. The ultrapolar electrosurgery blade assembly of claim 1 wherein the non-conductive hollow tubular member comprises a ceramic.

6. The ultrapolar electrosurgery blade assembly of claim 1 wherein the non-conductive blade comprises a ceramic.

7. The ultrapolar electrosurgery blade assembly of claim 1 wherein at least a portion of the active contact and the return contact are covered by the non-conductive hollow tubular member and project outward and downward from the narrow elongated top of the non-conductive blade.

8. The ultrapolar electrosurgery blade assembly of claim 1 wherein the non-conductive hollow tubular member includes a slot which fits over the narrow elongated top of the non-conductive blade.

9. The ultrapolar electrosurgery blade assembly of claim 8 wherein the non-conductive tubular member further includes an opening located above the slot on each end of the non-conductive tubular member.

10. An ultrapolar electrosurgery pencil with argon beam capability comprising:

a handpiece member having a first end and a second end;

a non-conductive blade positioned within the first end of the handpiece member wherein the non-conductive blade includes opposing planar sides, a sharp cutting end, and both an active contact and a return contact located on each of the opposing planar sides of the non-conductive blade;

a non-conductive hollow tubular member positioned on said non-conductive blade; and a non-conductive tube positioned within the handpiece member and connected to the non-conductive hollow tubular member for supplying a gas to the non-conductive hollow tubular member.

11. The ultrapolar electrosurgery pencil of claim 10 wherein the handpiece member includes a channel therein for evacuating at least one of smoke and debris away from the sharp cutting end of the non-conductive blade.

12. The ultrapolar electrosurgery pencil of claim 11 further comprising a rotating member connected to the second end of the handpiece member.

13. The ultrapolar electrosurgery pencil of claim 10 wherein the non-conductive hollow tubular member includes a slot which fits over the narrow elongated top of the non-conductive blade.

14. The ultrapolar electrosurgery pencil of claim 13 wherein the non-conductive tubular member further includes an opening located above the slot on each end of the non-conductive tubular member.

15. The ultrapolar electrosurgery pencil of claim 10 further comprising a second non-conductive hollow tubular member positioned between, and connected to, the non-conductive hollow tubular member and the non-conductive tube.

16. The ultrapolar electrosurgery blade of claim 15 wherein the hollow non-conductive tubular member is positioned outside of the first end of the handpiece member.

17. An ultrapolar electrosurgery blade assembly comprising:

a non-conductive blade having opposing planar sides, a narrow elongated top, a sharp cutting end, and an opposite non-cutting end;

both an active contact and a return contact located on each of the opposing planar sides of the non-conductive blade; and a non-conductive hollow tubular member positioned over the narrow elongated top of the non-conductive blade.

18. The ultrapolar electrosurgery blade assembly of claim 17 further comprising a non-conductive shelf support for supporting the non-conductive hollow tubular member when positioned over the narrow elongated top of the non-conductive blade.

19. The ultrapolar electrosurgery blade assembly of claim 17 further comprising a second non-conductive hollow tubular member positioned over the narrow elongated top of the non-conductive blade adjacent to the non-conductive hollow tubular member.

20. The ultrapolar electrosurgery blade assembly of claim 17 wherein the narrow elongated top of the non-conductive blade separates an active contact on one opposing planar side of the non-conductive blade and a return contact on the other opposing side of the non-conductive blade.

* * * * *